United States Patent [19]

Amitai et al.

[11] Patent Number: 4,675,326

[45] Date of Patent: Jun. 23, 1987

[54] BISQUATERNARY ANTIDOTES

[76] Inventors: Gabriel Amitai, 11 Aharoni St., Rehovot 76281; David Balderman, 13 Shinkin St., Givataim 53291; Rachel Bruckstein-Davidovici, 34 Emek Habracha St., Tel Aviv 67456, Israel; Michael Spiegelstein, Rehovot, all of Israel

[21] Appl. No.: 731,883

[22] Filed: May 8, 1985

[51] Int. Cl.$^4$ .................... A61K 31/46; C07D 401/12
[52] U.S. Cl. .................................... 514/304; 514/305; 514/318; 546/133; 546/137; 546/193; 546/194
[58] Field of Search ............... 546/137, 133, 193, 194; 514/305, 318, 304

[56] References Cited

U.S. PATENT DOCUMENTS

3,184,452   5/1965   Druey et al. .................... 546/193

OTHER PUBLICATIONS

March, J., *Advanced Organic Chemistry*, McGraw Hill, New York, 1968, pp. 331–332.
F. Mobbiger in *Handbuch der Experimentellen Pharmakologie*, O. Eichler et al. (Editors), Springer Verlag, Berlin, 1963, pp. 921–968.
H. Kewitz et al., *Arch. Biochem. Biophys.* 64, 456 (1956).
O. Wolthuis, et al., *Eur. J. Pharmacol.*, 49, 415 (1978).
G. Amitai, et al., *Biochem. Pharmacol.*, 29, 483 (1980).
J. Gordon, et al., *Toxicol. App. Pharmacol.*, 43, 207 (1978).
J. Schenk, et al., *Arch Toxicol.*, 36, 71 (1976).
M. D. Mashkovsky, *First Intern. Pharmacol. Meeting*, 7, 359 (1961).

*Primary Examiner*—Richard A. Schwartz
*Attorney, Agent, or Firm*—Stiefel, Gross, Kurland & Pavane

[57] ABSTRACT

A novel series of antidotes against organophosphorus poisoning having both anti-muscarinic activity and reactivation potency, were synthesized and evaluated for their pharmacological efficacy.

The compounds are bisquarternary oxybismethylene(or:trimethylene)-bis-N-heterocycles.

The N-heterocycles are comprised of 2,3 or 4 monosubstituted pyridines, 3-substituted quinuclidines and 4-substituted N-methylpiperidines (exclusive of both groups in one molecule designating a substituted pyridine ring). Some of the compounds display a remarkably low acute toxicity in mice.

These antidotes have been shown to be effective against poisoning by a variety of organophosphorus compounds as well as carbamates. The compounds are also of value as active ingredients in ophthalmic preparations.

11 Claims, No Drawings

BISQUATERNARY ANTIDOTES

BACKGROUND OF THE INVENTION

Mono and bispyridinium oximes such as 2-PAM-Cl (pyridine 2-aldoxime methyl chloride) and toxogonin (N,N'-oxydimethylene bis(pyridinium 4-aldoxime) dichloride), serve as potent reactivators of acetylcholinesterase (AChE) inhibited by organophosphates. [F. Hobbiger, In Handbuch der Experimentellen Pharmakologie XII, Cholinesterases and Anticholinesterase Agents, Ed. G. B. Koelle, Springer Verlag, Berlin, p.921 (1963)].

The rational design of pyridinium oximes (Kewitz et al. archives Biochem. Biophys. 64, 456 (1956) as potential antidotes for treatment of organophosphorus poisoning indeed resulted in effective therapeutic agents against intoxication by a wide variety of insecticides and nerve agents. However, both 2-PAM-Cl and toxogonin (in combination with atropine) provide only partial protection against Soman (O-pinacolyl methylphosphonofluoridate) as well as other organophosphates causing rapid aging of organophosphonyl-AChE.

A new series of bis-pyridinium oximes HS-3, HS-6, HI-6, HGG-12 and HGG-42 first synthesized by Prof. Hagedorn and her collaborators (in Freiburg, Germany) were shown to be effective against respiratory failure and neuromuscular blockade caused by soman in rats and mice [O. L. Wolthuis and L. A. Kepener, Europ. J. Pharmacol. 49, 415 (1978)].

The therapeutic effect of the latter bispyridinium derivatives however, could not be entirely attributed to reactivation of phosphorylated AChE. Recently we demonstrated that several bispyridinium oximes bind specifically to the muscarinic receptor in mouse brain. The binding potency of these antidotes ($K_1$ $10^{-4}$–$10^{-5}$M) was found to correlate well to the antimuscarinic efficiency in the guinea pig ileum assay [G. Amitai et al Biochem. Pharmacol. 29, 483 (1980)]. Pretreatment by a carbamate (e.g. pyridostigmine) followed by subsequent therapeutic application of cholinolytics (atropine and benactyzine) and an oxime reactivator(HS-6 or P2S) provided improved protection against soman (J. J. Gordon et al Toxicol. and Applied Pharmacol., 43, 207–216 (1978), J. Schenk et al. Arch. Toxicol. 36, 71–81 (1976).

The maximum protective ratio (P.R.)* against soman poisoning achieved by any presently available combined treatment regime is far from satisfactory.

*P.R.=($LD_{50}T$)/($LD_{50}$) where $LD_{50}T$ is the $LD_{50}$ in animals that were administered antidotal treatment.

SUMMARY OF THE INVENTION

In the present invention, we show a new approach where an antimuscarinic moiety is attached covalently to a known reactivator residue pyridinium-2-aldoxime. This structure is designed to achieve the following (a) An increase in the efficiency of the oxime by addition of another recognition factor to the molecule towards improved accessibility to the muscarinic receptor located at the postsynaptic (or presynaptic) membrane.

(b) Increasing the antimuscarinic (cholinolytic) activity of the oxime molecule thereby enhancing its antidotal efficacy.

(c) Directing the drug molecule to heterogeneous sub-population of muscarinic receptors other than those blocked by the anticholinergic glycolates (such as: atropine and benactyzine).

(d) To obtain a singular pharmacokinetic pattern by combining two moieties within one molecule.

In order to reduce the relative toxicity of the new compounds we selected derivatives containing antimuscarinic moieties, either clinically employed or commonly used in pharmacological research. A specific example for the selection of such moiety is 3-acetoxyquinuclidine (Aceclidine) used as an antiglaucoma drug. By converting the quinuclidine nitrogen to a quaternary derivative, Aceclidine is transformed into a compound with mild cholinolytic activity. [Mashkovsky, M. D. in: Modern Concepts in the Relationship between Structure and Pharmacological Activity. First Intern. Pharmacol. Meeting 7,359 (1961)]. This modification in the pharmacodynamic activity was demonstrated to exist to some extent also in other 3-substituted quinuclidine derivatives (Mashkovsky, M. D. ibid.) The general formula for the new compounds is presented by I:

wherein Q and Q' are selected from:

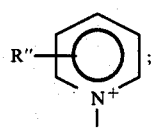

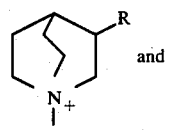

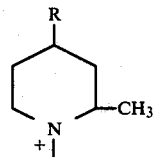

wherein Q and Q' moieties can be identical or different, with the exception of both groups designating a pyridine group (A),
wherein:
R designates

=O, —OR', alkoxy or aryloxy
R' designates hydrogen, alkyl, aralkyl or aryl
R" designates —HC=NOH or $CH_2R'$
W designates —O— or (—$CH_2$)—$_n$ where n=1–5
X designates Cl, Br or I
and wherein the R" group is located in the 2, 3 or 4 position of the pyridine ring.

PREPARATION OF THE NEW COMPOUNDS

The present invention also relates to a process for the production of the above mentioned novel compounds.

Compounds of the general Formula I can be prepared by three routes.

(a) The reaction of 1-(pyridiniumaldoxime) 3-chlorodimethylether chloride with the appropriate 3-quinuclidinyl or 4-N-methyl piperidyl derivative. The following scheme describes the synthetic route for the substituted quinuclidinyl (or 4-N-methyl piperidyl) derivative.

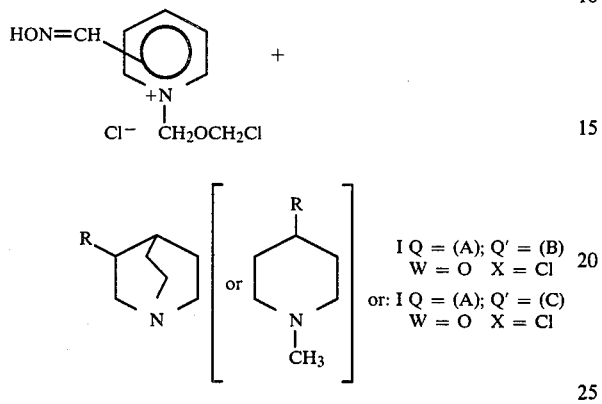

(b) The reaction of pyridine aldoxime with 1-(3-aryloxy) quinuclidinium) 3-chlorodimethyl ether chloride.

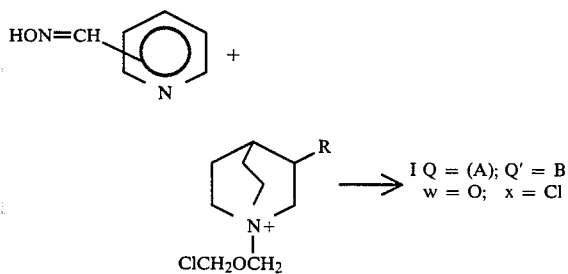

(c) The reaction of 1-(pyridiniumaldoxime)-3-bromopropyl bromide with an alkoxy or aryloxy quinuclidine derivative.

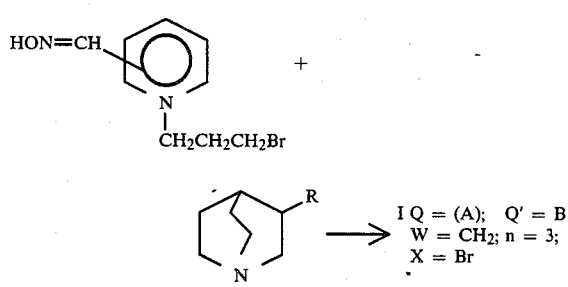

Compounds of the general formula I Q=(B) Q'=(C), Q=Q'(B) and Q=Q'=(C) were prepared according to the following general scheme:

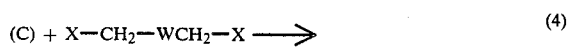

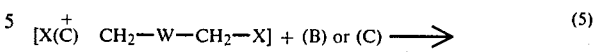

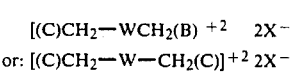

Where: (B) (C), W and X are as specified in general formula I.

Compounds of the general formula I, were prepared and NMR, mass-spectrum, and UV spectrum correlates well with the expected structures. The purity was checked by TLC. The preparation of the compounds of this invention is demonstrated in the following examples.

The melting points of the new compounds are summarized in Table I.

Example 1

1-(Pyridinium-2-aldoxime)-3-(3'-acetoxy quinuclidinium) dimethylether dichloride (AB-1)

I Q=(A) R''=CH=N'OH at position 2,

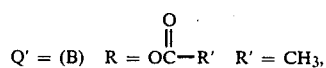

W=O, X=Cl

Step 1: Preparation of 1-(3'-acetoxy quinuclidine) 3-chloro dimethylether chloride.

1,3-Bischloromethylether (10 ml, 13.2 g. 0.11 mole) is dissolved in 100 ml dry chloroform. A solution of 3-acetoxyquinuclidine (10 g 0.06 mole) in 50 ml chloroform is added dropwise to the 1,3-bischloromethylether solution at room temperature with continuous stirring. The temperature rises to 50° C. and after cooling to room temperature the mixture is refluxed for another 3 hours. The solvent is evaporated under reduced pressure to yield the expected compound as a colorless viscous oil.

'H NMR (in CDCl₃) δppm: (relative to TMS) 2.2 singlet (3H); 1.75-2.7 multiplet (6H); 5.05-5.25 multiplet (1H); 5.5 singlet (2H); 5.85 singlet (2H).

Step 2: Preparation of 1-(pyridinium 2-aldoxime) 3-(3'-acetoxyquinuclidinium) dimethylether dichloride.

The product of Step 1 is used without any further purification for Step 2. It is dissolved in chloroform (14 g. 0.05 mole in 200 ml) and added into a solution of pyridine-2-aldoxime (20 g. 0.163 mole). The mixture is heated with continuous stirring and refluxed for 4 hours. A yellow solid precipitates in the solution. The mixture is cooled to room temperature and the solid is filtered off. (10 gr. 40%). The crude product is recrystallized in absolute ethanol and acetone to yield a white solid m.p. 135°-137° C. 'H NMR—(in D₂O) δppm (relative to DSS) 2.1 S. (3H) 1.75-2.75 m. (5H); 3.35-4.25 m. (6H); 5.0 S. (2H); 5.0-5.35 m. (1H); 6.5 S. (2H); 8.0-9.25 m. (4H); 8.75 S. (1H).

TLC (cellulose, Ethanol: 1N HCl, 1:1) reveals a single spot with R$_f$=0.86. A molecular peak in the form of a monoquaternary ion (dication-H⁺) obtained in the secondary ion mass spectrum (SIMS) technique at m/z=335.

EXAMPLE 2

1,3Bis(3-hydroxyimino quinuclidinium) dimethylether dichloride (AB-6) (I, Q=Q'=(B), R===N—OH, W=O, X=Cl)

3-hydroxyimino quinuclidine (17 g., 0.12 mole) is added into 100 ml dry acetone which contains 1,3-bis-chloromethylether (7 g. 0.06 mole).

The heterogeneous mixture is refluxed for 15 hours with continuous stirring. The crude product (10 g, 46%) was filtered and recrystallized in methanol-acetone, m.p. 240°–245° C. TLC (cellulose, ethanol=HCl (1N), 1:1) reveals a single spot with $R_f$=0.70.

$^1$H NMR (in $D_2O$) δppm (relative to DSS) 2.2–3 m. (10H); 3.5–4 m. (8H); 4.5 S. (4H) 5.2 S. (4H).

Example 3

1-(pyridinium-4-aldoxime 3-(3'-benzyloxyquinuclidinium trimethylene dibromide (I, Q=(A), R"=—CH=NOH at position 4) (AB-5)

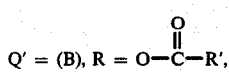

$R'=C_6H_5$, W=$CH_2$, X=Br; n=3

A solution of 3-benzyloxyquinuclidine (3.5 g, 0.015 mole) in 50 ml absolute ethanol was added dropwise to a solution of 1-(pyridinium-4-aldoxime) 3-bromo trimethylene bromide (6.5 g, 2.02 mole) in 200 ml absolute ethanol. The homogeneous solution was refluxed for 6 hours and a yellow oily precipitate was formed. The solvent was decanted and the crude product was triturated with dry diethylether. After evaporating the ether the yellow solid is recrystallized in isopropanol-ether (2 g. 24%) m.p.=95°–98° C. TLC (silica gel chloroform-methanol 4:1) reveals a single spot with $R_f$=0.3.

$^1$H NMR (in $D_2O$) (δppm relative to DSS) 1.2 g (2H), 2.0–4.0 m. (2H+2H+11H) 7.5–8.5 m. (4H aromatic+1H methene).

Pharmacological and Biochemical Properties of the New Compounds:

(1) The $LD_{50}$ values for the acute toxicity of the new compounds are summarized in Table II. Some compounds (e.g. AB-8 and AB-13) display a remarkable low toxicity in mice (2144 and 1124 μmole/kg, respectively). The marked low toxicity of AB-8 and AB-13 renders these novel drugs suitable for the safe treatment of organophosphorus poisoning and other medical uses (such as opthalmological preparations). They may be administered in amounts of, desirably, from about 5 to about 100 mg/kg by weight.

(2) General signs observed during pharmacological screening in mice (doses: 0.4–0.5×$LD_{50}$) were:
(a) slight mydriasis;
(b) decreased motor activity;
(c) decreased respiratory rate.

(3) The efficacy of different treatments in mice against poisoning by various organophosphates is summarized in Table III. Sign-free doses of AB-1, AB-8 and AB-13 in combination with atropine and benactyzine were administered by i.m. injection after poisoning with either soman, sarin or VX. In the case of soman poisoning pretreatment with pyridostigmine was essential. The efficiency of the novel drugs was compared to TMB-4 administered together with atropine and benactyzine. AB-1, AB-8 and AB-13 were superior to TMB-4 in the treatment of soman poisoning. AB-8 and AB-13 were comparable to TMB-4 in their antidotal activity against sarin, AB-13 was slightly better than TMB-4 in the treatment against VX.

(4) The antidotal efficiency of AB-8 and AB-13 in the treatment of insecticide poisoning is summarized in Table IV. Mice were challenged with either Paraoxon (diethyl p-nitrophenyl phosphate) or the carbamate Temik (2-methyl 2-(methylthio) propionaldehyde O-(methyl)-carbamoyl oxime. AB-13 displayed a protection ratio (in combination with atropine) which was higher than TMB-4 (in combination with atropine) in the treatment of both Paraoxon and Temik.

(5) The affinity constants ($K_1$) for the binding of AB-1, AB-8, AB-13 and AB-14 to the mascarinic receptor (rat brain homogenate) are summarized in Table V. It is noteworthy that the $K_I$ value obtained for AB-1 is 30-fold smaller than the $K_I$ for N-methylaceclidine ($1.2 \times 10^{-4}$M) [F. J. Ehlert and D. J. Jenden Mol. Pharmacol. 25, 46–50 (1984)]. This result indicates that combining the quaternary aceclidine moiety with pyridinealdoxime enhances the affinity to the [$^3$H] QNB binding site. The AB compounds are also mild antagonists of the muscarinic receptor as measured by blocking the effect of acetylcholine on isolated guinea-pig ileum (not shown). However, one cannot rule out other putative mechanisms for the antidotal action of the novel compounds such as antinicotinic activity and/or presynaptic effects: either blocking acetylcholine release or inhibition of high affinity uptake of choline.

(6) The reactivation of diethylphosphoryl-AChE by some of the novel drugs was measured using the Ellman procedure for determining AChE activity (G. L. Ellman, K. D. Courtney, V. Andres and R. M. Featherstone Biochem. Pharmacol. 7, 88 (1961)). Reactivation potency was determined by measuring the bimolecular rate constant of reactivation ($k_r$). The $k_r$ values obtained for: Toxogonin, AB-13, AB-8, AB-1 and AB-14 are: $7.18.10^4$, $2.51.10^4$, $1.82 \cdot 10^2$, 47.2 $M^{-1}$ $min^{-1}$ respectively. (25° C., 0.1M phosphate pH 7.0).

AChE (electric ell) was initially inhibited by diethylphosphorochloridate. Subsequently, the diethylphosphoryl-AChE conjugate was diluted into the reactivation medium containing various concentrations of the reactivator. The kinetic scheme and processing of the experimental data were described previously by Y. Ashani and S. Cohen J. Med. Chem. 14, 621 (1971).

TABLE I

The New Derivatives, Melting Points and Synthetic Procedures

| No. | Code Name | Q | Q' | HC=NOH position | W | R | X | m.p. °C. | Example Procedure No. |
|-----|-----------|---|----|-----------------|----|---|---|----------|----------------------|
| 1 | AB-1 | (A) | (B) | 2 | O | —OC(=O)—CH$_3$ | —Cl | 135-7 | 1 |

TABLE I-continued

The New Derivatives, Melting Points and Synthetic Procedures

| No. | Code Name | Q | Q' | HC=NOH position | W | R | X | m.p. °C. | Example Procedure No. |
|---|---|---|---|---|---|---|---|---|---|
| 2 | AB-2 | (A) | (B) | 2 | O | $-OCC_6H_5$ (O=) | Cl | 115-20 | 1 |
| 3 | AB-3 | (A) | (B) | 3 | O | $-OCCH_3$ (O=) | Cl | 153-5 | 1 |
| 4 | AB-4 | (A) | (B) | 4 | O | $-OCCH_3$ (O=) | Cl | 200-205 | 1 |
| 5 | AB-5 | (A) | (B) | 4 | CH$_2$ | $-OCC_6H_5$ (O=) | Br[c] | 95-98 | 3 |
| 6 | AB-6 | (B) | (B) | — | O | =N—OH | Cl | 240-5 | 2 |
| 7 | AB-7 | (A) | (B) | 4 | CH$_2$ | —OH | Br[c] | [b] | 3 |
| 8 | AB-8 | (A) | (B) | 2 | O | =O | Cl | 155-7 | 1 |
| 9 | AB-9 | (A) | (C) | 2 | O | $-OCCH_3$ (O=) | Cl | 145-50 | 1 |
| 10 | AB-10 | (A) | (B) | 2 | O | —OH | Cl | 170-71 | 1 |
| 11 | AB-11 | (A) | (B) | 4 | CH$_2$ | =O | Br[c] | [b] | 3 |
| 12 | AB-13 | (A) | (B) | 4 | O | =O | Cl | 172-5 | 1 |
| 13 | AB-14 | (A)[d] | (B) | —[d] | O | =O | Cl | 185 dec. | 1 |

[a] All melting points were determined on a Thomas-Hoover 6427-H10 apparatus and are uncorrected.
[b] Highly hygroscopic
[c] All bromide salts were recrystallized in isopropanol-ether.
[d] The pyridine ring is substituted by a methyl group at position 2.

TABLE II

Acute Toxicity of the New Compounds. (i.m. male mice, ICR-England)

| No. | Code Name | LD$_{50}$ (mg/Kg) | 95% Confidence Limit[a] | LD$_{50}$ ($\mu$mole/Kg) |
|---|---|---|---|---|
| 1 | AB-1 | 290.0 | 229:0; 365.0 | 714 |
| 2 | AB-2 | 99.7 | 98.6; 100.4 | 213 |
| 3 | AB-3 | 136.5 | 112.2; 169.8 | 336 |
| 4 | AB-4 | 267.9 | 263.6; 274.6 | 659 |
| 5 | AB-5 | 7.6 | 6.0; 9.5 | 13 |
| 6 | AB-6 | 268.0 | 198.0; 366.0 | 678 |
| 7 | AB-7 | 167.9 | 138.0; 208.9 | 372 |
| 8 | AB-8 | 776.2 | 676.1; 891.2 | 2144 |
| 9 | AB-9 | 316.2 | 239.9; 418.4 | 802 |
| 10 | AB-10 | 263.0 | — | 722 |
| 11 | AB-13 | 407.4 | 354.8; 467.7 | 1124 |
| 12 | AB-14 | 331.1 | 288.4; 380.2 | 994 |
| 13 | TMB-4[b] | 69.8 | 56.3; 82.2 | 167 |
| 14 | TOXOGONIN[b] | 145.0 | 128. 157 | 404 |

[a] LD$_{50}$ - data was processed according to C.S. Weil Biometrics 8, 249-263 (1952).
[b] J. G. Clement, Fundam. Appl. Toxicol. 1, 193-202 (1981).

TABLE III

Efficacy of Different Treatments Against Organophosphorus Poisoning in Mice

| PRETREATMENT | | O-P Poison (S.C.) | Time after poisoning (sec) | TREATMENT (mg/kg i.m.) | | | | | | Protection Ratio |
|---|---|---|---|---|---|---|---|---|---|---|
| Time Min. | Pyridostigmine (i.m. 130 mg/kg) | | | Atropine | Benactyzine | TMB-4 | AB-1 | AB-8 | AB-13 | |
| 30 | + | Soman | 10 | 11.2 | 8.0 | — | 50 | — | — | 6.4 (5.6; 8.5) |
| 30 | + | " | 10 | 11.2 | 8.0 | — | — | — | 100 | 6.0(4.6; 7.9) |
| 30 | + | " | 10 | 11.2 | 8.0 | — | — | 150 | — | 7.3(6.0; 8.8) |
| 30 | + | " | 10 | 11.2 | 8.0 | 12.6 | — | — | — | 3.4(2.5; 4.6) |
| 30 | + | Sarin | 10 | 11.2 | 8.0 | — | 50 | — | — | 6.2(5.3; 7.1) |
| — | — | " | 10 | 11.2 | 8.0 | — | 50 | — | — | 3.3(2.4; 4.6) |
| — | — | " | 10 | 11.2 | — | — | — | — | 100 | 7.1(6.5; 7.8) |
| — | — | " | 10 | 11.2 | 8.0 | — | — | — | 100 | 6.6(3.4; 12.9) |
| 30 | + | " | 10 | 11.2 | 8.0 | — | — | 150 | — | 11.5(9.5; 13.8) |
| — | — | " | 10 | 11.2 | 8.0 | — | — | 150 | — | 7.3(6; 8.7) |
| — | — | " | 10 | 11.2 | — | — | — | 150 | — | 6.8(5.7; 8.0) |
| — | — | " | 10 | 11.2 | 8.0 | 12.6 | — | — | — | 8.4(5.6; 8.7) |
| — | — | VX | 60 | 11.2 | 8.0 | — | 50 | — | — | 9.7(8.9; 10.5) |

TABLE III-continued

Efficacy of Different Treatments Against Organophosphorus Poisoning in Mice

| PRETREATMENT | | O-P Poison (S.C.) | Time after poisoning (sec) | TREATMENT (mg/kg i.m.) | | | | | | Protection Ratio |
|---|---|---|---|---|---|---|---|---|---|---|
| Time Min. | Pyridostigmine (i.m. 130 mg/kg) | | | Atropine | Benactyzine | TMB-4 | AB-1 | AB-8 | AB-13 | |
| — | — | " | 60 | 11.2 | 8.0 | — | — | — | 100 | 43.5(31.5; 60.0) |
| — | — | " | 60 | 11.2 | 8.0 | — | — | 150 | — | 13.5(7.9; 22.7) |
| — | — | " | 60 | 11.2 | 8.0 | 12.6 | — | — | — | 36.2(29.4; 44.5) |

TABLE IV

Antidotal Efficiency of AB-8 and AB-13 against Insecticide Poisoning in Mice

| Insecticide | Therapeutic Mixture (mg/Kg)[a] | | | | Protection Ratio (95% Confidence Limit) |
|---|---|---|---|---|---|
| | AB-13 | AB-8 | Atropine | TMB-4 | |
| Paraoxon[b] | 100 | — | 11.2 | — | 25.7 (18.2; 36.3) |
| | — | 150 | 11.2 | — | 8.7 (4.5; 17) |
| | — | — | 11.2 | 12.6 | 14.1 (12.0; 16.6) |
| Temik[c] | 100 | — | 11.2 | — | 19.8 (—) |
| | — | 150 | 11.2 | — | 30.0 (25.1; 35.6) |
| | — | — | 11.2 | 12.6 | 5.8 (4.6; 7.3) |

[a]The therapeutic mixture was injected one minute after poisoning the mice.
[b]Diethyl p-nitrophenyl phosphate (Paraoxon) was dissolved in propylene glycol.
[c]2-methyl 2-(methylthio) propionaldehyde O-(methylcarbamoyl)oxime (Temik) was dissolved in saline.

TABLE V

Inhibition of [³H]QNB Binding to the Muscarinic Receptor of Rat Brain Homogenate[a] by the new compounds

| No. | Code Name | $K_I (\times 10^5)$ M[b] |
|---|---|---|
| 1 | AB-1 | 0.4 ± 0.1 |
| 2 | AB-8 | 5.6 ± 1.6 |
| 3 | AB-13 | 7.9 ± 1.0 |
| 4 | AB-14 | 4.0 ± 1.8 |

[a]The homogenate was suspended in 0.05 M Na₂HPO₄—KH₂PO₄ pH 7.4 and binding was measured at 25° C.
[b]$K_I$ was calculated according to the following equation:

$$K_I = \frac{IC_{50}}{\Delta + \frac{L}{K_D}}$$

where:
$IC_{50}$, is the concentration of ligand that causes 50% decrease in (³H)QNB binding
L = 2 nM, concentration of [³H]QNB (L-(Benzilic-4,4'-³H(N) quinuclidinyl benzilate, 33.1 ci/mmole New England Nuclear Corp. Boston MA).
$K_D$ = Dissociation constant for [³H]-L-QNB determined under identical conditions (0.08 nM)

We claim:
1. A compound of the formula

$$Q-CH_2-W-CH_2-Q'2X^-$$

wherein
Q is

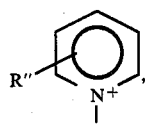
(A)

Q' is selected from the group consisting of

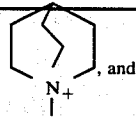
(B)

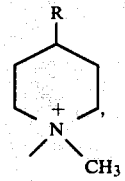
(C)

and
R is

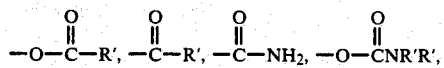

=N—OH, =O, OR', lower alkoxy or phenoxy;
R' is —H, loweralkyl, phenylloweralkyl or phenyl;
W is —O— or —(CH₂)ₙ—; (n=1-5);
X is a physiologically acceptable anion;
R" is OH—N=CH— or CH₂R' and wherein the R" group is located in the 2, 3 or 4 position on the pyridine ring.

2. A compound according to claim 1, wherein the group Q is a group (A) and Q' is a group (B).

3. A compound according to claim 1, wherein the group Q is a group (A) and Q' is a group (C).

4. A compound according to claim 1, wherein R designates acetoxy and R" designates CH=N—OH in the 3-position.

5. A compound according to claim 1, where the group R designates a group =O, =N—OH or —O—C-(O)R', wherein R' is as defined in claim 1.

6. A compound according to claim 1, wherein W is —O—.

7. A compound according to claim 1, wherein W is —(CH₂)ₙ— and n=1 to 5.

8. A pharmaceutical antidote composition against poisoning by organo phosphorus or carbamate compounds, comprising a pharmaceutically acceptable carrier and as an active ingredient, a therapeutically effective dose of a compound claimed in claim 1.

9. An antidote composition according to claim 8, which additionally contains an effective quantity of atropine and/or benactyzine.

10. An opthalmic preparation comprising a pharmaceutically acceptable carrier and as an active ingredient, a therapeutically effective dose of a compound as defined in claim 1.

11. A method of treating a mammal against poisoning by organo phosphorus or carbamate compounds comprising administering the antidote composition of claim 8 to the mammal in such quantity that the amount of the active compound of the composition is in the range of about 5 to about 100 mg/kg by weight of said mammal.

* * * * *